(12) United States Patent
Watson

(10) Patent No.: US 8,079,991 B2
(45) Date of Patent: Dec. 20, 2011

(54) WOUND SUCTION PEG APPARATUS

(75) Inventor: Richard L. Watson, McPherson, KS (US)

(73) Assignee: KCI Licensing Inc., San Antonio, TX (US)

( * ) Notice: Subject to any disclaimer, the term of this patent is extended or adjusted under 35 U.S.C. 154(b) by 726 days.

(21) Appl. No.: 11/807,631

(22) Filed: May 30, 2007

(65) Prior Publication Data

US 2008/0033401 A1    Feb. 7, 2008

Related U.S. Application Data

(60) Provisional application No. 60/803,716, filed on Jun. 2, 2006.

(51) Int. Cl.
*A61M 1/00* (2006.01)
(52) U.S. Cl. .................. 604/313; 604/315; 604/543
(58) Field of Classification Search .......... 604/313–315, 604/543
See application file for complete search history.

(56) References Cited

U.S. PATENT DOCUMENTS

| | | |
|---|---|---|
| 1,355,846 A | 10/1920 | Rannells |
| 2,547,758 A | 4/1951 | Keeling |
| 2,632,443 A | 3/1953 | Lesher |
| 2,682,873 A | 7/1954 | Evans et al. |
| 2,910,763 A | 11/1959 | Lauterbach |
| 2,969,057 A | 1/1961 | Simmons |
| 3,066,672 A | 12/1962 | Crosby, Jr. et al. |
| 3,367,332 A | 2/1968 | Groves |
| 3,520,300 A | 7/1970 | Flower, Jr. |
| 3,568,675 A | 3/1971 | Harvey |
| 3,648,692 A | 3/1972 | Wheeler |
| 3,682,180 A | 8/1972 | McFarlane |
| 3,826,254 A | 7/1974 | Mellor |
| 4,080,970 A | 3/1978 | Miller |
| 4,096,853 A | 6/1978 | Weigand |
| 4,139,004 A | 2/1979 | Gonzalez, Jr. |
| 4,165,748 A | 8/1979 | Johnson |
| 4,184,510 A | 1/1980 | Murry et al. |

(Continued)

FOREIGN PATENT DOCUMENTS

AU    550575 A1    8/1982

(Continued)

OTHER PUBLICATIONS

Louis C. Argenta, MD and Michael J. Morykwas, PhD; "Vacuum-Assisted Closure: A New Method for Wound Control and Treatment: Clinical Experience"; Annals of Plastic Surgery, vol. 38, No. 6, Jun. 1997; pp. 563-576.

(Continued)

*Primary Examiner* — Lynne Anderson

(57) ABSTRACT

An apparatus is provided for placement in a wound to treat and promote healing of the wound by suctioning unwanted fluids and debris from the wound. The apparatus includes a suction head peg made of multi-fibered material that is soft-enable in the human body by body fluids. A membrane and cuff are included for attachment to the body, and a suction tube is in operable communication with the suction head peg and a suction pump to provide suction at the suction head peg. While the stiffened peg is capable of insertion into the body, it is designed to soften in fluid such as the body fluids with which the peg comes into contact after insertion into the wound or abscess. This softening allows the peg to change shape and conform to the shrinking wound or abscess cavity as material is suctioned therefrom.

20 Claims, 2 Drawing Sheets

U.S. PATENT DOCUMENTS

| | | | |
|---|---|---|---|
| 4,233,969 A | 11/1980 | Lock et al. | |
| 4,245,630 A | 1/1981 | Lloyd et al. | |
| 4,246,899 A | 1/1981 | Loseff | |
| 4,256,109 A | 3/1981 | Nichols | |
| 4,261,363 A | 4/1981 | Russo | |
| 4,275,721 A | 6/1981 | Olson | |
| 4,284,079 A | 8/1981 | Adair | |
| 4,297,995 A | 11/1981 | Golub | |
| 4,333,468 A | 6/1982 | Geist | |
| 4,373,519 A | 2/1983 | Errede et al. | |
| 4,382,441 A | 5/1983 | Svedman | |
| 4,392,853 A | 7/1983 | Muto | |
| 4,392,858 A | 7/1983 | George et al. | |
| 4,419,097 A | 12/1983 | Rowland | |
| 4,465,485 A | 8/1984 | Kashmer et al. | |
| 4,475,909 A | 10/1984 | Eisenberg | |
| 4,480,638 A | 11/1984 | Schmid | |
| 4,525,166 A | 6/1985 | Leclerc | |
| 4,525,374 A | 6/1985 | Vaillancourt | |
| 4,540,412 A | 9/1985 | Van Overloop | |
| 4,543,100 A | 9/1985 | Brodsky | |
| 4,548,202 A | 10/1985 | Duncan | |
| 4,551,139 A | 11/1985 | Plaas et al. | |
| 4,569,348 A | 2/1986 | Hasslinger | |
| 4,605,399 A | 8/1986 | Weston et al. | |
| 4,608,041 A | 8/1986 | Nielsen | |
| 4,640,688 A | 2/1987 | Hauser | |
| 4,655,754 A | 4/1987 | Richmond et al. | |
| 4,664,662 A | 5/1987 | Webster | |
| 4,710,165 A | 12/1987 | McNeil et al. | |
| 4,733,659 A | 3/1988 | Edenbaum et al. | |
| 4,743,232 A | 5/1988 | Kruger | |
| 4,758,220 A | 7/1988 | Sundblom et al. | |
| 4,787,888 A | 11/1988 | Fox | |
| 4,826,494 A | 5/1989 | Richmond et al. | |
| 4,838,883 A | 6/1989 | Matsuura | |
| 4,840,187 A | 6/1989 | Brazier | |
| 4,863,449 A | 9/1989 | Therriault et al. | |
| 4,872,450 A | 10/1989 | Austad | |
| 4,878,901 A | 11/1989 | Sachse | |
| 4,897,081 A | 1/1990 | Poirier et al. | |
| 4,906,233 A | 3/1990 | Moriuchi et al. | |
| 4,906,240 A | 3/1990 | Reed et al. | |
| 4,919,654 A | 4/1990 | Kalt | |
| 4,941,882 A | 7/1990 | Ward et al. | |
| 4,953,565 A | 9/1990 | Tachibana et al. | |
| 4,969,880 A | 11/1990 | Zamierowski | |
| 4,985,019 A | 1/1991 | Michelson | |
| 5,037,397 A | 8/1991 | Kalt et al. | |
| 5,085,633 A * | 2/1992 | Hanifl et al. | 604/35 |
| 5,086,170 A | 2/1992 | Luheshi et al. | |
| 5,092,858 A | 3/1992 | Benson et al. | |
| 5,100,396 A | 3/1992 | Zamierowski | |
| 5,134,994 A | 8/1992 | Say | |
| 5,149,331 A | 9/1992 | Ferdman et al. | |
| 5,151,404 A | 9/1992 | Suzuki et al. | |
| 5,167,613 A | 12/1992 | Karami et al. | |
| 5,176,663 A | 1/1993 | Svedman et al. | |
| 5,215,522 A | 6/1993 | Page et al. | |
| 5,232,453 A | 8/1993 | Plass et al. | |
| 5,261,893 A | 11/1993 | Zamierowski | |
| 5,278,100 A | 1/1994 | Doan et al. | |
| 5,279,550 A | 1/1994 | Habib et al. | |
| 5,298,015 A | 3/1994 | Komatsuzaki et al. | |
| 5,342,376 A | 8/1994 | Ruff | |
| 5,344,415 A | 9/1994 | DeBusk et al. | |
| 5,358,494 A | 10/1994 | Svedman | |
| 5,437,622 A | 8/1995 | Carion | |
| 5,437,651 A | 8/1995 | Todd et al. | |
| 5,453,099 A | 9/1995 | Lee et al. | |
| 5,527,293 A | 6/1996 | Zamierowski | |
| 5,549,584 A | 8/1996 | Gross | |
| 5,556,375 A | 9/1996 | Ewall | |
| 5,607,388 A | 3/1997 | Ewall | |
| 5,636,643 A | 6/1997 | Argenta et al. | |
| 5,645,081 A | 7/1997 | Argenta et al. | |
| 5,911,222 A * | 6/1999 | Lawrence et al. | 600/574 |
| 6,071,267 A | 6/2000 | Zamierowski | |
| 6,135,116 A | 10/2000 | Vogel et al. | |
| 6,159,240 A | 12/2000 | Sparer et al. | |
| 6,241,747 B1 | 6/2001 | Ruff | |
| 6,287,316 B1 | 9/2001 | Agarwal et al. | |
| 6,345,623 B1 | 2/2002 | Heaton et al. | |
| 6,488,643 B1 | 12/2002 | Tumey et al. | |
| 6,493,568 B1 | 12/2002 | Bell et al. | |
| 6,553,998 B2 | 4/2003 | Heaton et al. | |
| 6,752,794 B2 * | 6/2004 | Lockwood et al. | 604/313 |
| 6,814,079 B2 | 11/2004 | Heaton et al. | |
| 6,979,324 B2 * | 12/2005 | Bybordi et al. | 604/313 |
| 2002/0077661 A1 | 6/2002 | Saadat | |
| 2002/0115951 A1 | 8/2002 | Norstrem et al. | |
| 2002/0120185 A1 | 8/2002 | Johnson | |
| 2002/0143286 A1 | 10/2002 | Tumey | |
| 2005/0107756 A1 | 5/2005 | McCraw | |
| 2006/0041247 A1 | 2/2006 | Petrosenko et al. | |
| 2007/0027414 A1 | 2/2007 | Hoffman et al. | |

FOREIGN PATENT DOCUMENTS

| | | |
|---|---|---|
| AU | 745271 | 4/1999 |
| AU | 755496 | 2/2002 |
| CA | 2005436 | 6/1990 |
| DE | 26 40 413 A1 | 3/1978 |
| DE | 43 06 478 A1 | 9/1994 |
| DE | 295 04 378 U1 | 10/1995 |
| DE | 10 2005 010 419 A1 | 9/2006 |
| EP | 0100148 A1 | 2/1984 |
| EP | 0117632 A2 | 9/1984 |
| EP | 0161865 A2 | 11/1985 |
| EP | 0358302 A2 | 3/1990 |
| EP | 1018967 B1 | 8/2004 |
| EP | 1 415 671 A1 | 5/2007 |
| GB | 692578 | 6/1953 |
| GB | 2 195 255 A | 4/1988 |
| GB | 2 197 789 A | 6/1988 |
| GB | 2 220 357 A | 1/1990 |
| GB | 2 235 877 A | 3/1991 |
| GB | 2 333 965 A | 8/1999 |
| GB | 2 329 127 B | 8/2000 |
| GB | 2 409 412 A | 6/2005 |
| JP | 03-188844 | 8/1991 |
| JP | 4129536 | 4/1992 |
| JP | 05-277176 | 10/1993 |
| SG | 71559 | 4/2002 |
| WO | WO 80/02182 | 10/1980 |
| WO | WO 87/04626 | 8/1987 |
| WO | WO 90/10424 | 9/1990 |
| WO | WO 93/09727 | 5/1993 |
| WO | WO 93/14724 A1 | 8/1993 |
| WO | WO 94/20041 | 9/1994 |
| WO | WO 96/05873 | 2/1996 |
| WO | WO 97/18007 | 5/1997 |
| WO | WO 99/13793 | 3/1999 |
| WO | WO 2006/005939 A1 | 1/2006 |

OTHER PUBLICATIONS

Susan Mendez-Eastmen, RN; "When Wounds Won't Heal" RN Jan. 1998, vol. 61 (1); Medical Economics Company, Inc., Montvale, NJ, USA; pp. 20-24.

James H. Blackburn, II, MD, et al; "Negative-Pressure Dressings as a Bolster for Skin Grafts"; Annals of Plastic Surgery, vol. 40, No. 5, May 1998, pp. 453-457.

John Masters; "Reliable, Inexpensive and Simple Suction Dressings"; Letter to the Editor, British Journal of Plastic Surgery, 1998, vol. 51 (3), p. 267; Elsevier Science/The British Association of Plastic Surgeons, UK.

S.E. Greer, et al "The Use of Subatmospheric Pressure Dressing Therapy to Close Lymphocutaneous Fistulas of the Groin" British Journal of Plastic Surgery (2000), 53, pp. 484-487.

George V. Letsou, MD., et al; "Stimulation of Adenylate Cyclase Activity in Cultured Endothelial Cells Subjected to Cyclic Stretch"; Journal of Cardiovascular Surgery, 31, 1990, pp. 634-639.

Orringer, Jay, et al; "Management of Wounds in Patients with Complex Enterocutaneous Fistulas"; Surgery, Gynecology & Obstetrics, Jul. 1987, vol. 165, pp. 79-80.

International Search Report for PCT International Application PCT/GB95/01983; Nov. 23, 1995.
PCT International Search Report for PCT International Application PCT/GB98/02713; Jan. 8, 1999.
PCT Written Opinion; PCT International Application PCT/GB98/02713; Jun. 8, 1999.
PCT International Examination and Search Report, PCT International Application PCT/GB96/02802; Jan. 15, 1998 & Apr. 29, 1997.
PCT Written Opinion, PCT International Application PCT/GB96/02802; Sep. 3, 1997.
Dattilo, Philip P., Jr., et al; "Medical Textiles: Application of an Absorbable Barbed Bi-directional Surgical Suture"; Journal of Textile and Apparel, Technology and Management, vol. 2, Issue 2, Spring 2002, pp. 1-5.
Kostyuchenok, B.M., et al; "Vacuum Treatment in the Surgical Management of Purulent Wounds"; Vestnik Khirurgi, Sep. 1986, pp. 18-21 and 6 page English translation thereof.
Davydov, Yu. A., et al; "Vacuum Therapy in the Treatment of Purulent Lactation Mastitis"; Vestnik Khirurgi, May 14, 1986, pp. 66-70, and 9 page English translation thereof.
Yusupov. Yu. N., et al; "Active Wound Drainage", Vestnik Khirurgi, vol. 138, Issue 4, 1987, and 7 page English translation thereof.
Davydov, Yu. A., et al; "Bacteriological and Cytological Assessment of Vacuum Therapy for Purulent Wounds"; Vestnik Khirurgi, Oct 1988, pp. 48-52, and 8 page English translation thereof.
Davydov, Yu. A., et al; "Concepts for the Clinical-Biological Management of the Wound Process in the Treatment of Purulent Wounds by Means of Vacuum Therapy"; Vestnik Khirurgi, Jul. 7, 1980, pp. 132-136; and 8 page English translation thereof.
Chariker, Mark E., M.D., et al; "Effective Management of incisional and cutaneous fistulae with closed suction wound drainage"; Contemporary Surgery, vol. 34, Jun. 1989, pp. 59-63.
Egnell Minor, Instruction Book, First Edition, 300 7502, Feb. 1975, pp. 24.
Egnell Minor: Addition to the Users Manual Concerning Overflow Protection—Concerns all Egnell Pumps, Feb. 3, 1983, pp. 2.
Svedman, P.: "Irrigation Treatment of Leg Ulcers", The Lancet, Sep. 3, 1983, pp. 532-534.
Chinn, Steven D. et al.: "Closed Wound Suction Drainage", The Journal of Foot Surgery, vol. 24, No. 1, 1985, pp. 76-81.
Arnljots, Björn et al.: "Irrigation Treatment in Split-Thickness Skin Grafting of Intractable Leg Ulcers", Scand J. Plast Reconstr. Surg., No. 19, 1985, pp. 211-213.
Svedman, P.: "A Dressing Allowing Continuous Treatment of a Biosurface", IRCS Medical Science: Biomedical Technology, Clinical Medicine, Surgery and Transplantation, vol. 7, 1979, p. 221.
Svedman, P. et al.: "A Dressing System Providing Fluid Supply and Suction Drainage Used for Continuous or Intermittent Irrigation", Annals of Plastic Surgery, vol. 17, No. 2, Aug. 1986, pp. 125-133.
N.A. Bagautdinov, "Variant of External Vacuum Aspiration in the Treatment of Purulent Diseases of the Soft Tissues," *Current Problems in Modern Clinical Surgery: Interdepartmental Collection*, edited by V. Ye Volkov et al. (Chuvashia State University, Cheboksary, U.S.S.R. 1986);pp. 94-96.
K.F. Jeter, T.E. Tintle, and M. Chariker, "Managing Draining Wounds and Fistulae: New and Established Methods," *Chronic Wound Care*, edited by D. Krasner (Health Management Publications, Inc., King of Prussia, PA 1990), pp. 240-246.
G. Živadinović, V. Dukić, Ž. Maksimović, D. Radak, and P. Peška, "Vacuum Therapy in the Treatment of Peripheral Blood Vessels," *Timok Medical Journal* 11 (1986), pp. 161-164.
F.E. Johnson, "An Improved Technique for Skin Graft Placement Using a Suction Drain," *Surgery, Gynecology, and Obstetrics* 159 (1984), pp. 584-585.
A.A. Safronov, Dissertation Abstract, *Vacuum Therapy of Trophic Ulcers of the Lower Leg with Simultaneous Autoplasty of the Skin* (Central Scientific Research Institute of Traumatology and Orthopedics, Moscow, U.S.S.R. 1967).
M. Schein, R. Saadia, J.R. Jamieson, and G.A.G. Decker, "The 'Sandwich Technique' in the Management of the Open Abdomen," *British Journal of Surgery* 73 (1986), pp. 369-370.
D.E. Tribble, An Improved Sump Drain-Irrigation Device of Simple Construction, *Archives of Surgery* 105 (1972) pp. 511-513.
M.J, Morykwas, L.C. Argenta, E.I. Shelton-Brown, and W. McGuirt, "Vacuum-Assisted Closure: A New Method for Wound Control and Treatment: Animal Studies and Basic Foundation," *Annals of Plastic Surgery* 38 (1997), pp. 553-562 (Morykwas I).
C.E. Tennants, "The Use of Hypermia in the Postoperative Treatment of Lesions of the Extremities and Thorax," *Journal of the American Medical Association* 64 (1915), pp. 1548-1549.
Selections from W. Meyer and V. Schmieden, *Bier's Hyperemic Treatment in Surgery, Medicine, and the Specialties: A Manual of Its Practical Application*, (W.B. Saunders Co., Philadelphia, PA 1909), pp. 17-25, 44-64, 90-96, 167-170, and 210-211.
International Search Report and Written Opinion dated Oct. 23, 2008; International Patent Application No. PCT/US07/12881.
European Search Report date mailed Feb. 25, 2011 for European Application No. 07809266.5.

\* cited by examiner

WOUND SUCTION PEG APPARATUS

CROSS-REFERENCE TO RELATED APPLICATION

This application claims the benefit of and priority to U.S. Provisional Application No. 60/803,716, filed Jun. 2, 2006, which is hereby incorporated by reference.

BACKGROUND OF THE INVENTION

1. Field of the Invention

Applicants' invention relates generally to a device in the wound healing arts. More particularly, it relates to a novel wound healing apparatus having a multi-fibered peg for acting a suction head for removing excess fluid from a wound.

2. Description of Related Art

A wound cavity, such as a seroma, is sometimes created in human flesh after the removal of a bulk of tissue during surgery or other invasive trauma to the body. Such interior cavities commonly develop after the surgery is completed and the skin is closed. A need exists for a system and method that will treat these cavities, and like wound and abscess cavities such as those that arise due to infection.

BRIEF SUMMARY OF THE INVENTION

The present invention is directed to an apparatus for placement in a wound to treat and promote healing of the wound by suctioning unwanted fluids and debris from the wound. The apparatus preferably comprises a suction head peg made of multi-fibered material that is softenable in the human body by body fluids.

The device has a head unit that is designed to be placed on the patient's body, generally over the wound area. The head unit is anticipated to take a number of forms, but in a first embodiment is comprised of a membrane and cuff for attachment to the body, a suction tube in operable communication with a suction pump (or communicable with a suction pump), and the peg, which is in operable communication with the suction tube. The suction tube may be removably attachable to the remainder of the head unit via a connector. A suction line is continuous through the suction tube, the peg, and the remainder of the head unit, and the suction line provides the operative communication for the components.

The peg is made from a stiffened material that is capable of being inserted through the epidermal, scar, scab, and other tissue that can close or cover a wound or abscess. While the stiffened peg is capable of insertion, it is designed to soften in fluid such as the body fluids it comes into contact with after insertion into the wound or abscess. This softening allows the peg to change shape and conform to the shrinking wound or abscess cavity as material is suctioned therefrom. This conforming actions helps limits the unwanted penetration by a peg that does not soften and conform into the good tissue surrounding the wound/abscess cavity.

The suction tube, or tubes, serve as conduits to remove fluids from the wound, preferably under the power of a suction device to which the tubes are connected outside the body. The peg acts as the tip of that suction apparatus. During the healing process, the suction tube serves as a conduit to remove excess fluid from the wound through the suction tube. Preferably, the suction tube is connected to a suction device such as a vacuum pump (not shown) outside the body to facilitate removal of excess fluid from the cavity.

The present apparatus and method may be used with animals as well as humans.

DETAILED DESCRIPTION OF THE PREFERRED EMBODIMENT

In the following detailed description of the preferred embodiments, reference is made to the accompanying drawings which form a part hereof, and in which is shown by way of illustration specific preferred embodiments in which the invention may be practiced. These embodiments are described in sufficient detail to enable those skilled in the art to practice the invention, and it is understood that other embodiments may be utilized and that logical mechanical, structural, and chemical changes may be made without departing from the spirit or scope of the invention. To avoid detail not necessary to enable those skilled in the art to practice the invention, the description may omit certain information known to those skilled in the art. The following detailed description is, therefore, not to be taken in a limiting sense, and the scope of the present invention is defined only by the appended claims.

Figure 1:
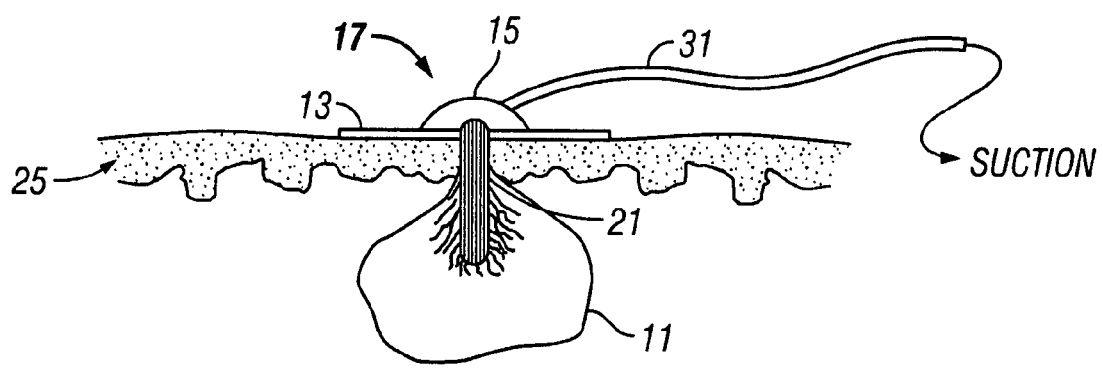
FIG. 1 is a side view of a first embodiment of the present invention deployed into a wound cavity.

Referring to the figures, FIG. 1 illustrates an embodiment of the present invention inserted into a wound abscess cavity 11. The membrane 13 and cuff 15 make up a part of the head unit 17 and sit on the surface of the body, with the peg 21, or suction tip, inserted through the skin layer 25 and into the abscess cavity 11. The peg 21 is hollow and has one or more apertures or pores. The apertures and pores are in communication with the suction line 31 through the head unit 17. Suction applied through the peg 21 pulls body fluids and debris in the abscess cavity 11 into the peg pores or apertures and through the suction line 31, draining the abscess cavity 11.

The initial insertion of the peg 21 is facilitated due to the peg 21 being stiffened. This stiffening of the peg 21 may be a natural characteristic of the material used in the manufacture of the peg 21, or it may induced through the use of stiffening agent applied to the peg 21. The stiffening agent is anticipated to be a starch, complex carbohydrate, or gelatin, but other substances that exhibit the necessary stiffening in air and softening in fluid characteristics may be used as well. An anticipated alternative is that a flexible peg 21 could be used in conjunction with the stiffening agent, and the stiffening agent be one that simply dissolves in the presence of fluids leaving the flexible peg 21 in the abscess, rather than the stiffening agent itself softening.

Figure 2:
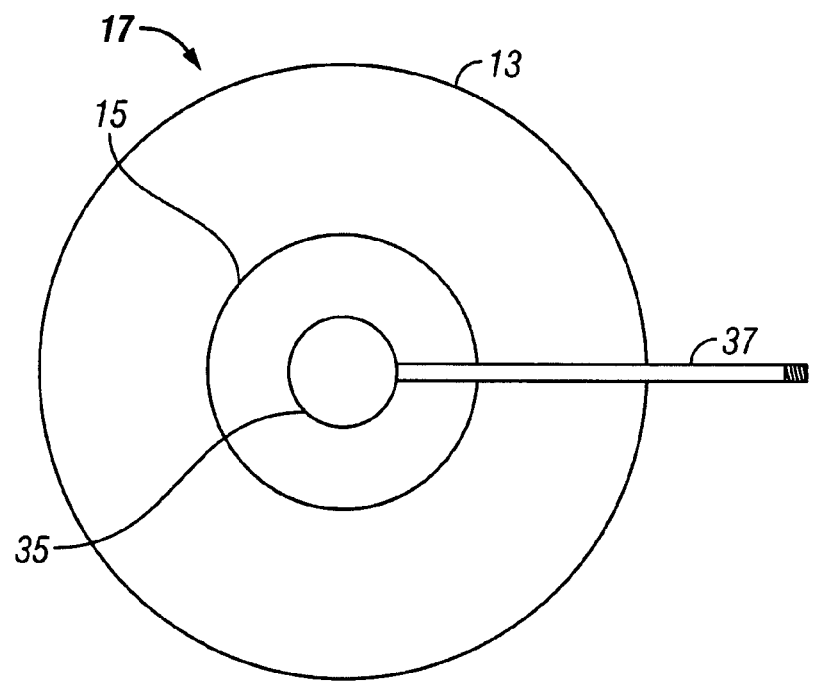
FIG. 2 is a top view of a second embodiment of the present invention deployed into a wound cavity.

FIG. 2 shows the present invention with a flange 35 and connector 37 that allows for the attachment of the suction tube 31. The cuff 15 and membrane 13 can be attached to the skin in a variety of ways such as a strap or adhesives, or they may simply sit on top of the skin and allow the peg 21 to hold the unit in place.

Figure 3:
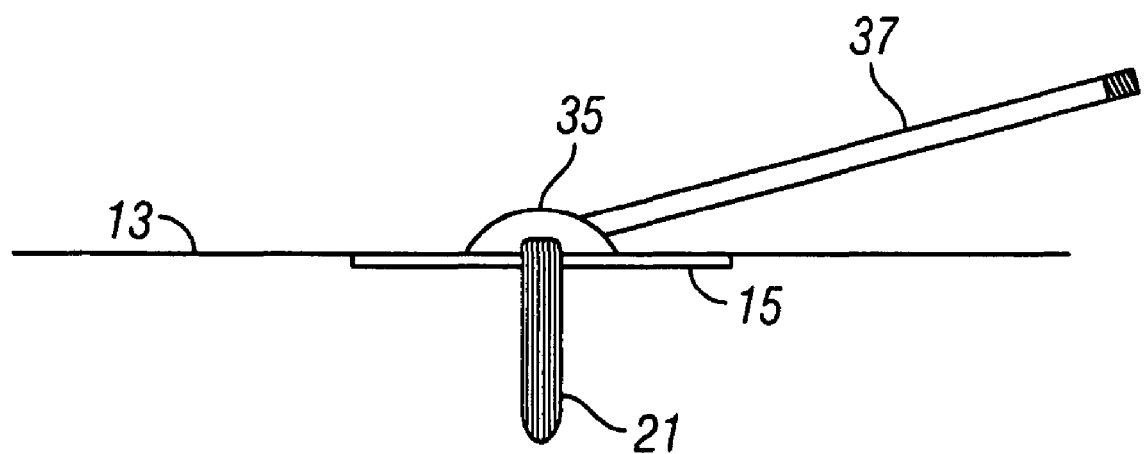
FIG. 3 is a side view of a second embodiment of the present invention deployed into a wound cavity.

FIG. 3 shows the present invention with the suction tube disconnected from the connector. The peg is anticipated to be made from a multi-fibered material that provides enough stiffness to allow the peg to puncture the tissue and debris over the abscess cavity. It also provides the apertures necessary to allow for suction of the fluid and debris in the wound to be suctioned into the suction line. The peg is anticipated to be hollow along its longitudinal axis to allow for communication with the suction line. Although there are many materials that the peg could be fashioned from, some of those that are anticipated to be used are silicone, polytetrafluoroethylene sold under the name Teflon™, plastic, and like fibers or meshes.

As persons of ordinary skill in the art will appreciate, materials may be used in lieu of or in addition to the above described peg and stiffening agent in accordance with the present invention.

Although the invention has been described with reference to specific embodiments, this description is not meant to be construed in a limited sense. Various modifications of the disclosed embodiments, as well as alternative embodiments of the inventions will become apparent to persons skilled in the art upon the reference to the description of the invention. It is, therefore, contemplated that the appended claims will cover such modifications that fall within the scope of the invention.

I claim:

1. A wound suction apparatus for suctioning fluid and debris from a wound cavity, the apparatus comprising:
    a suction tip comprised of a fibrous material having sufficient stiffness to penetrate tissue covering the wound cavity and that softens in the presence of fluid;
    a cuff enclosing the suction tip within the wound cavity; and
    a suction line in fluid communication with the fibrous suction tip.

2. The apparatus of claim 1, wherein the suction tip has a peg shape having a longitudinal axis along which is disposed a channel.

3. The apparatus of claim 2, wherein the suction tip further comprises a plurality of apertures in fluid communication with the channel.

4. The apparatus of claim 1, further comprising:
    a channel disposed along a longitudinal axis of the suction tip;
    a pump; and
    wherein the suction line includes a first end connected to the pump and a second end connected to the channel.

5. The apparatus of claim 4, wherein the suction tip further comprises a plurality of apertures in fluid communication with the channel.

6. The apparatus of claim 1, further comprising:
    a channel disposed along a longitudinal axis of the suction tip;
    a vacuum pump; and
    wherein the suction line includes a first end connected to the vacuum pump and a second end connected to the channel.

7. The apparatus of claim 1, further comprising:
    a flange covering the cuff;
    a connector attached to the flange;
    a pump; and
    a suction line having a first end connected to the vacuum pump and a second end connected to the connector.

8. The apparatus of claim 1, wherein the fibrous material has sufficient stiffness due to the presence of a stiffening agent, the stiffening agent adapted to soften in the presence of fluid.

9. The apparatus of claim 1, wherein the fibrous material has sufficient stiffness due to the presence of a stiffening agent, the stiffening agent adapted to dissolve in the presence of fluid.

10. The apparatus of claim 1, wherein the fibrous material has sufficient stiffness due to the presence of a starch.

11. The apparatus of claim 1, wherein the fibrous material has sufficient stiffness due to the presence of a complex carbohydrate.

12. The apparatus of claim 1, wherein the fibrous material has sufficient stiffness due to the presence of a gelatin.

13. The apparatus of claim 1, wherein the fibrous material is comprised of silicone fibers.

14. The apparatus of claim 1, wherein the fibrous material is comprised of polytetrafluoroethylene fibers.

15. The apparatus of claim 1, wherein the fibrous material is comprised of plastic fibers.

16. The apparatus of claim 1, further comprising:
    a stiffening agent applied to the fibrous material, the stiffening agent adapted to soften in the presence of fluid;
    a channel disposed along a longitudinal axis of the suction tip;
    a pump; and
    wherein the suction line includes a first end connected to the pump and a second end connected to the channel.

17. The apparatus of claim 1, further comprising:
    a stiffening agent applied to the fibrous material, the stiffening agent adapted to soften in the presence of fluid;
    a channel disposed along a longitudinal axis of the suction tip;
    a pump;
    wherein the suction line includes a first end connected to the pump and a second end connected to the channel; and
    wherein the fibrous material is comprised of fibers selected from a group consisting of silicone fibers, polytetrafluoroethylene fibers, and plastic fibers.

18. A system for suctioning fluid and debris from a wound cavity, the system comprising:
    a suction tip comprised of a fibrous material;
    a means for stiffening the fibrous material sufficient to penetrate tissue covering the wound cavity;
    a means for softening the fibrous material in the presence of fluid; and
    a means for securing the suction tip in the wound cavity.

19. The system of claim 18, further comprising:
    a means for drawing fluid from the wound cavity through the suction tip; and
    a means for connecting the suction tip to the means for drawing fluid.

20. A method for treating a wound cavity, the method comprising:
    inserting a fibrous peg into the wound cavity;
    softening the fibrous peg in the wound cavity in the presence of fluid;
    connecting the fibrous peg to a conduit; and
    withdrawing fluid through the fibrous peg into the conduit.

* * * * *